United States Patent [19]  [11] 4,057,564
Youngdale  [45] Nov. 8, 1977

[54] 2a,2b-DIHOMO-15-ALKYL-PGE$_2$ ANALOGS

[75] Inventor: Gilbert A. Youngdale, Portage, Mich.

[73] Assignee: The Upjohn Company, Kalamazoo, Mich.

[21] Appl. No.: 663,566

[22] Filed: Mar. 3, 1976

Related U.S. Application Data

[62] Division of Ser. No. 511,220, Oct. 2, 1974, Pat. No. 3,974,195.

[51] Int. Cl.$^2$ ............................................. G07C 177/00
[52] U.S. Cl. .............................. 260/410.9 R; 260/404; 260/413
[58] Field of Search .............. 260/468 D, 514 D, 404, 260/410.9 R, 413

[56] References Cited

U.S. PATENT DOCUMENTS

| 3,514,383 | 5/1970 | Beal et al. | 204/158 |
| 3,816,393 | 6/1974 | Hayashi et al. | 260/209 |
| 3,904,679 | 9/1975 | Bundy | 260/514 |

*Primary Examiner*—Robert Gerstl
*Attorney, Agent, or Firm*—Robert A. Armitage

[57] ABSTRACT

2a,2b-Dihomo-15-methyl and 15-ethyl PGF- and PGE-type compounds are disclosed with processes for making them. These compounds are useful for a variety of pharmacological purposes, including anti-ulcer, inhibition of platelet aggregation, increase of nasal patency, labor inducement at term, and wound healing.

7 Claims, No Drawings

2A,2B-DIHOMO-15-ALKYL-PGE₂ ANALOGS

The present application is a division of Ser. No. 551,220, filed Oct. 10, 1974, issued on Aug. 10, 1976 as U.S. Pat. 3,974,195.

The present invention relates to prostaglandin analogs, the essential material constituting a disclosure of which is incorporated here by reference from U.S. Pat. 3,974,195.

I claim:

1. An optically active compound of the formula:

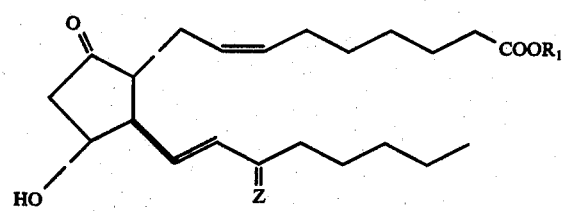

wherein Z is

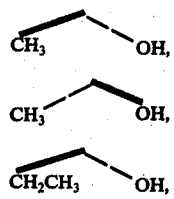

or

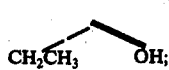

and wherein $R_1$ is hydrogen, alkyl of one to 12 carbon atoms, inclusive,

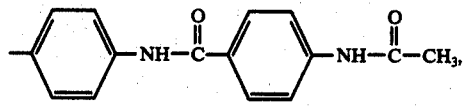

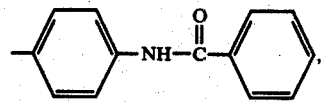

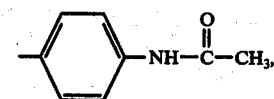

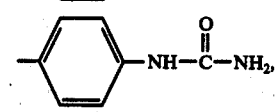

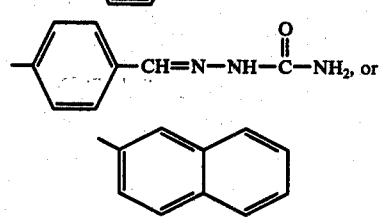

or pharmacologically acceptable salts thereof when $R_1$ is hydrogen.

2. A compound according to claim 1, wherein Z is

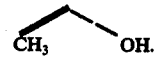

3. 2a,2b-Dihomo-15(S)-15-methyl-PGE₂, a compound according to claim 2, wherein $R_1$ is hydrogen.

4. 2a,2b-Dihomo-15(S)-15-methyl-PGE₂, methyl ester, a compound according to claim 2, wherein $R_1$ is methyl.

5. A compound according to claim 1, wherein Z is

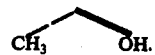

6. 2a,2b-Dihomo-15(R)-15-methyl-PGE₂, a compound according to claim 5, wherein $R_1$ is hydrogen.

7. 2a,2b-Dihomo-15(R)-15-methyl-PGE₂, methyl ester, a compound according to claim 5, wherein $R_1$ is methyl.

* * * * *